United States Patent
Bates et al.

(10) Patent No.: US 6,808,682 B1
(45) Date of Patent: Oct. 26, 2004

(54) ASSAYING DEVICE CONSISTING OF THE TEST CARTRIDGE OR CASSETTE WITH A CAP OR COVER WHICH ATTACHES ONTO THE CARTRIDGE OR CASSETTE TO COVER AND SEAL THE WELL OR OPENING INTO WHICH THE SAMPLE HAS BEEN DEPOSITED

(75) Inventors: E. Alan Bates, Allison Park, PA (US); Jeffrey Kovalik, Bethel Park, PA (US); Gary Hoffman, Pittsburgh, PA (US)

(73) Assignee: Dtx, Inc., Pittsburgh, PA (US)

( * ) Notice: Subject to any disclaimer, the term of this patent is extended or adjusted under 35 U.S.C. 154(b) by 0 days.

(21) Appl. No.: 08/935,629

(22) Filed: Sep. 23, 1997

(51) Int. Cl.[7] .............................................. G01N 33/48
(52) U.S. Cl. ......................... 422/58; 422/61; 436/165; 436/169; 435/305.3; 435/305.4
(58) Field of Search ............................ 422/56, 58, 61, 422/102, 99–100, 103–104; 436/164, 165, 166, 169, 174, 808; 206/528, 538, 539; 435/287.1, 304.1, 304.2, 305.3, 305.4

(56) References Cited

U.S. PATENT DOCUMENTS

| | | | |
|---|---|---|---|
| 2,785,057 A | * | 3/1957 | Schwab et al. ............... 422/58 |
| 3,884,641 A | * | 5/1975 | Kraffczyk et al. ............ 422/56 |
| 4,624,929 A | * | 11/1986 | Ullman ....................... 436/179 |
| 4,981,786 A | * | 1/1991 | Dafforn et al. .............. 422/102 |
| 5,380,492 A | * | 1/1995 | Seymour ...................... 422/56 |
| 5,504,013 A | * | 4/1996 | Senior ......................... 422/56 |
| 5,683,659 A | * | 11/1997 | Hovatter ...................... 422/56 |
| 5,897,840 A | * | 4/1999 | Owens et al. ............... 422/102 |
| 5,962,336 A | * | 10/1999 | Sun .............................. 422/61 |
| 5,976,895 A | * | 11/1999 | Cipkowski .................. 422/102 |

FOREIGN PATENT DOCUMENTS

WO          97/33519     *   9/1997

* cited by examiner

*Primary Examiner*—Lyle A. Alexander

(57) ABSTRACT

An assaying device composed of a test cartridge/cassette and cap/cover. When attached, the cap/cover seals the top of a sample well/opening on the cartridge/cassette in a fluid tight manner, to protect from contact with and contamination of the tested sample (for example, urine for drug testing), provide easier, cleaner handling of the test cartridge/cassette and prevent intermixing of another sample.

20 Claims, 4 Drawing Sheets

US 6,808,682 B1

ASSAYING DEVICE CONSISTING OF THE TEST CARTRIDGE OR CASSETTE WITH A CAP OR COVER WHICH ATTACHES ONTO THE CARTRIDGE OR CASSETTE TO COVER AND SEAL THE WELL OR OPENING INTO WHICH THE SAMPLE HAS BEEN DEPOSITED

BACKGROUND

This invention generally relates to assaying devices and in particular the on-site immunoassay technology used to detect the presence of drugs in urine. On-site drug tests generally use an immunoassay method called antigen-antibody competitive binding to screen for the presence of drugs. Among the test kits used for such testing there are tests composed of a housing or container which contains a reagent test strip, an opening in which test results are displayed and a place for deposit of the sample. The sample wicks up into the reagent test strip and the results are displayed. The results are generally available within a few minutes. Often it is desirable to make a photocopy of the results, whether positive or negative, for a permanent record, since test results will change or disappear over time.

Possible problems include spilling of the sample, contamination of the sample, and contact by the test administrator or others with the sample during handling. A method is needed for a cleaner, more sanitary and easier handling of the test housing during and after the test administration, especially since specimens can be infectious. In order to photocopy the results, the test device is placed face down on the copier, so it is desirable to insure that sample will not leak onto the copier. Also a method is needed to insure a second sample from another donor is not inadvertently placed in the same test cartridge/cassette.

SUMMARY OF THE INVENTION

The housing or cartridge/cassette of the present invention will have one or two openings or "windows" in which the test results are displayed and one or two wells or openings in the top of the cartridge/cassette for deposit of the sample. The sample is placed in the well/opening by use of a pipette. The results will be displayed in the window. The cartridge/cassette and the cap or cover of the present invention will prevent the sample used in the test from spilling out, will prevent contamination of the sample, and will permit cleaner, more sanitary and easier handling of the cartridge/cassette during and after the wicking test process. The cap/cover when placed on the cartridge/cassette will provide a fluid tight relationship. The cartridge/cassette with the cap/cover provide a compact, easy to handle unit. The cap/cover if placed on the cartridge/cassette as soon as the sample begins wicking will prevent inadvertent commingling or intermixing of another sample.

It is the principal object of this invention to provide a convenient, compact, easily managed device for the containment of the sample.

It is also a further objective to provide a means to protect the sample from contamination once placed into the test well/opening.

It is a further objective to provide a means to protect the test administrator from undesirable contact with the sample while handling the test cartridge during the test administration.

It is a further objective to provide a means to protect the test administrator or others from undesirable contact with the sample during subsequent handling of the test cartridge.

It is a further objective of the present invention to provide a means of insuring that while photocopying the test results displayed in the test cartridge/cassette the sample will not leak from the well/opening onto the copier.

It is a further objective of the present invention to provide a means to prevent the test administrator from inadvertently commingling or intermixing a second sample from another donor.

These and other objects of the present invention will become readily apparent upon further review of the following specifications and drawings.

DETAILED DESCRIPTION OF THE INVENTION

Figure 1:
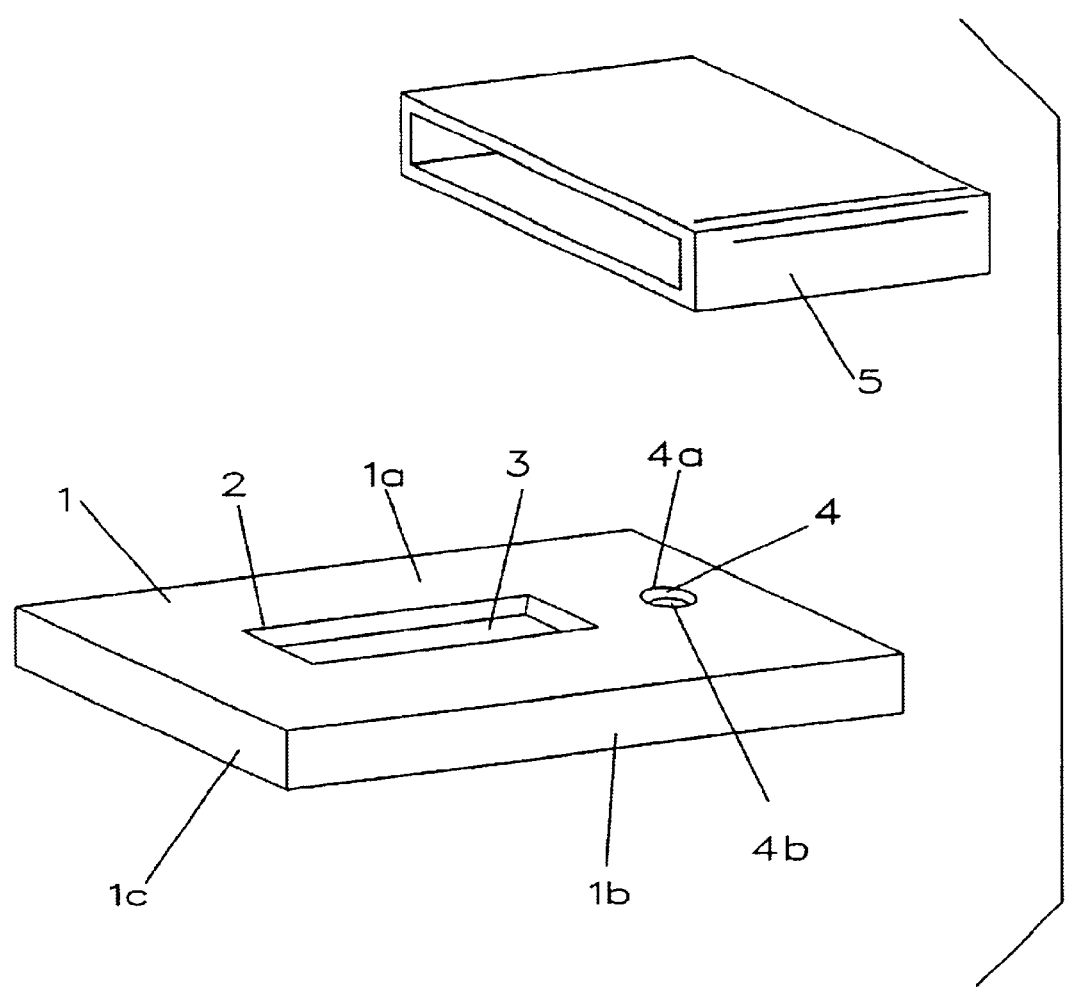
FIG. 1 is a perspective view of the cartridge/cassette and cap/cover separately as seen from the front or top.

FIG. 1 is a perspective view of the cartridge/cassette and cap/cover separately as seen from the front or top. The cartridge/cassette 1 contains an opening or window 2 in which the results on the test strip 3 will be displayed. As viewed in FIG. 1, cartridge/cassette 1 shows a broad, lateral face 1a, a narrow, lateral face 1b, and a narrow end face 1c. The sample will be dropped into the well/opening 4 on lateral face 1a, by means of a pipette. Well/opening 4, which is separate from window 2, has a top in the area of top edge 4a and extends from there into the cartridge/cassette to surround empty pace 4b for reception of the sample. The cap/cover 5 has not been placed onto the cartridge/cassette yet.

Figure 2:
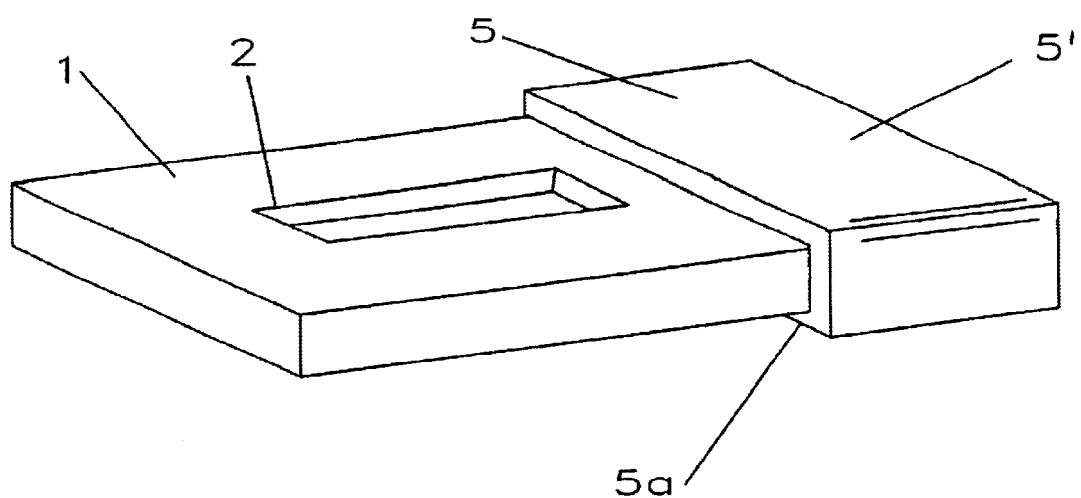
FIG. 2 is a perspective view of the cartridge/cassette and cap/cover snapped or slipped together as seen from the front.

FIG. 2 is a perspective view showing the cartridge/cassette and cap/cover snapped or slipped together following deposit of the sample. FIG. 2 is a view as seen from the front or top. The cartridge/cassette 1 with the results window 2 has the cap/cover 5 snapped or slipped into place. The sample well/opening, 4 in the other Figures, is now covered and sealed by the cap/cover 5 in a fluid tight relationship. In sealing, wall 5' of cap/cover 5 faces the face 1a containing the well/opening 4 and contacts the top of the well/opening. By sealing the top of the sample well/opening, the cap/cover 5 transforms space 4b into a chamber for retention of sample while the sample wicks for the test. As indicated by the cap/cover region 5a showing in FIG. 2, when assembled with the cartridge/cassette passes around, and, in fact, encircles, the cartridge/cassette, in order to hold the cap/cover in a fluid tight relationship against the top of the sample well/opening.

Figure 3:
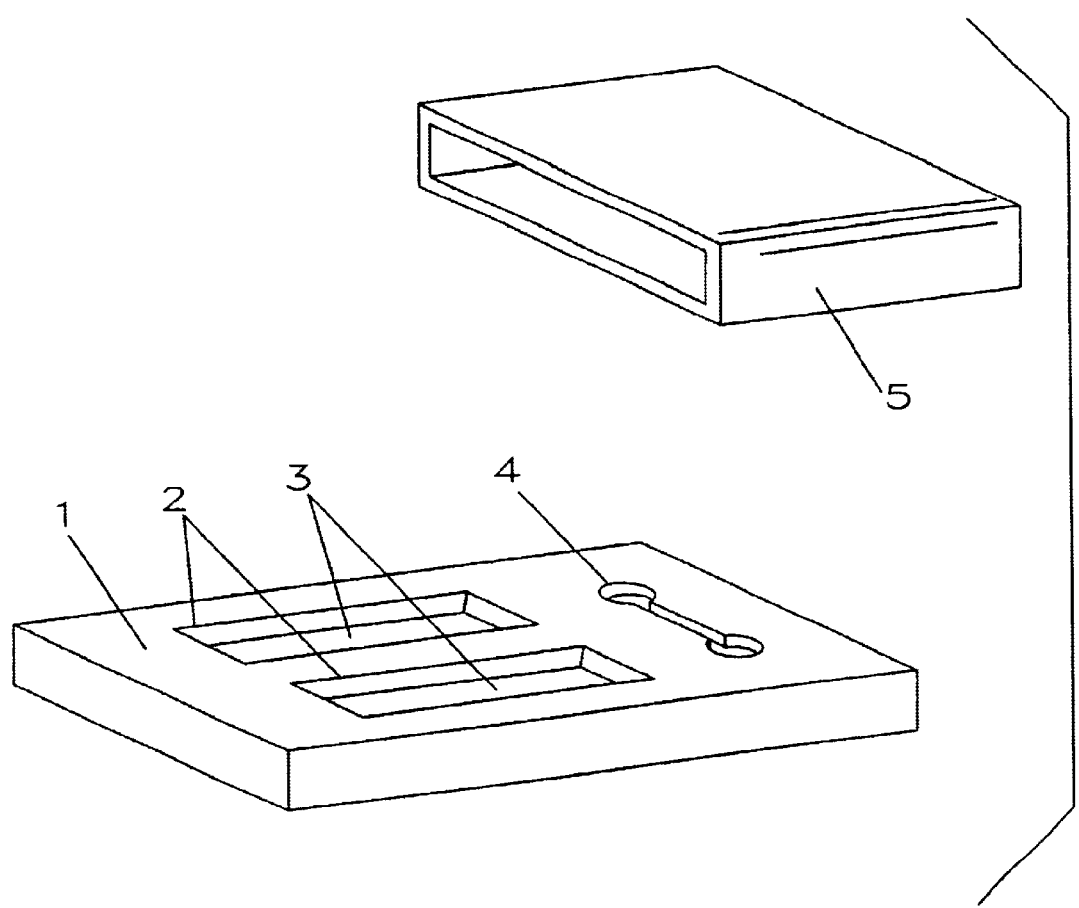
FIG. 3 is a perspective view of the cartridge/cassette with two windows and two sample well/openings and the cap/cover separately as seen from the front or top.

FIG. 3 shows a cartridge/cassette 1 with two results windows 2, two test strips 3, two sample well/openings with a connecting channel 4 and a separate cap/cover 5. This type of cartridge/cassette will accommodate more separate tests and requires a greater quantity of the sample.

Figure 4:
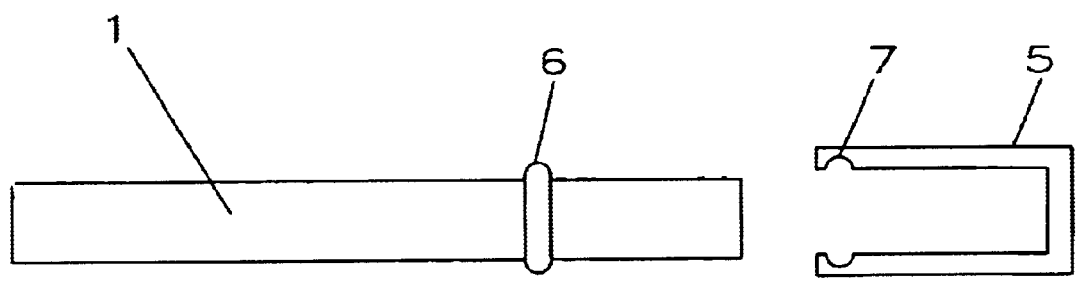
FIG. 4 is a side view of the cartridge/cassette and of the cap/cover (shown in cross section) showing the addition of edges on the cartridge/cassette and indentations on the cap/cover for further securing the cap/cover.

FIG. 4 shows a side view of the invention with the side of the cap/cover 5 cut away. The cartridge/cassette 1 is designed with a raised edge 6 and the cap/cover (shown in cross section) with indentations 7 which when snapped together will further insure the attachment.

Figure 5:
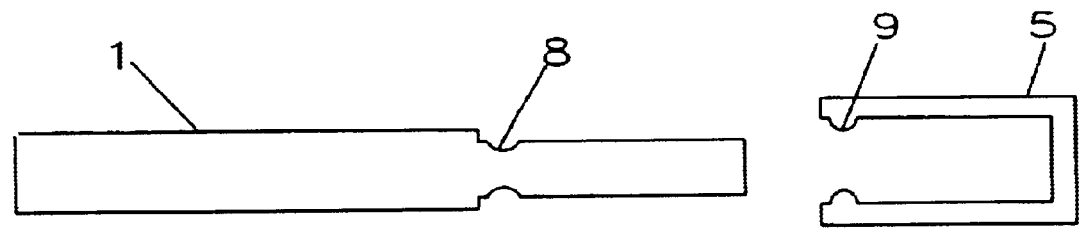
FIG. 5 is a side view of the cartridge/cassette and of the cap/cover (shown in cross section) showing the addition of indentations on the cartridge/cassette and raised buttons on the cap/cover for further securing the cap/cover.

FIG. 5 shows a side view of the invention with these of the cap/cover 5 cut away. The cartridge/cassette 1 is designed with an indentation 8 and the cap/cover (shown in cross section) with a raised button 7 which when snapped together will further insure the attachment. The end of the cartridge/cassette where the well/opening is located has been reduced in thickness with the result that when the cap/cover is attached it will be flush with the edges of the cassette/cover.

What is claimed is new and to be protected as set forth in the appended claims. Obviously although the embodiments described herein are the preferred one, modifications can be made to the shape of the cartridge/cassette and the cap/cover, without departing from the spirit and scope of this invention. The cartridge/cassette and the cap/cover may be formed or molded from any suitable material, usually plastic or other similar material, but the invention should work as well with most drug test materials. The cap is effective if it slips onto the cartridge/cassette snugly enough to insure that it will cover and seal the top of the sample well in a fluid tight relationship and will not detach. Raised buttons or edges can also be incorporated into the design of the cartridge/cassette and cap/cover to further insure that the cap/cover when snapped or slipped into place will not detach from the cartridge/cassette. The number of windows and urine well/openings shown are currently available, but more will not depart from the spirit and scope of this invention.

What is claimed are:

1. An assaying device for depositing and analyzing a sample, comprising:
   a. a cartridge/cassette means which contains a test strip, a window for viewing test results and a well/opening consisting essentially of an empty chamber separate from the window, having a top and serving for deposit of the sample; and
   b. a cap/cover means for sealing the top of the sample well/opening in a fluid tight relationship following deposit of the sample; the well/opening being situated on a broad, lateral face of the cartridge/cassette means; and the cap/cover means when sealing the top of the sample well/opening completely encircling the cartridge/cassette means, in order to hold the cap/cover means in a fluid tight relationship against the top of the sample well/opening.

2. An assaying device as claimed in claim 1, the cartridge/cassette means having a raised edge and the cap/cover means having indentations, the raised edge and the indentations, when snapped together, insuring the attachment of the cartridge/cassette means with the cap/cover means.

3. An assaying device as claimed in claim 1, the cartridge/cassette means having an indentation and the cap/cover means having a raised button, the indentation and button, when snapped together, insuring the attachment of the cartridge/cassette means with the cap/cover means.

4. An assaying device as claimed in claim 1, the cap/cover means having a wall which, in sealing, faces said face and contacts the top of the well/opening.

5. A method of using an assaying device as claimed in claim 1, comprising the steps of: depositing the sample into the well/opening; and attaching the cap/cover means to cover and seal the top of the well/opening in a fluid tight relationship.

6. A method as claimed in claim 5, further comprising, following the step of attaching, the additional steps of placing the cartridge/cassette on a photocopier and photocopying test results showing in the window.

7. An assaying device as claimed in claim 1, the well/opening extending from its top into the cartridge/cassette means to form the chamber for reception of sample.

8. An assaying device as claimed in claim 7, the space being empty.

9. An assaying device as claimed in claim 7, the cap/cover means when sealing the top of the sample well/opening closing the chamber for retention of sample.

10. An assaying device as claimed in claim 1, the well/opening extending from its top into the cartridge/cassette means to form the chamber for reception of sample.

11. An assaying device as claimed in claim 10, the space being empty.

12. A method of using an assaying device as claimed in claim 10, comprising the steps of: dropping the sample in the form of urine into the well/opening; and attaching the cap/cover means to cover and seal the top of the well/opening in a fluid, tight relationship.

13. A method as claimed in claim 12, wherein the dropping is done from a pipette.

14. An assaying device as claimed in claim 10, the cap/cover means when sealing the top of the sample well/opening closing the chamber for retention of sample.

15. An assaying device as claimed in claim 14, the cap/cover means when sealing the top of the sample well/opening passing around the cartridge/cassette means, in order to hold the cap/cover means in a fluid tight relationship against the top of the sample well/opening.

16. An assaying device as claimed in claim 15, the cap/cover means when sealing the top of the sample well/opening completely encircling the cartridge/cassette means, in order to hold the cap/cover means in a fluid tight relationship against the top of the sample well/opening.

17. An assaying device for depositing and analyzing a sample, comprising:
   a. cartridge/cassette means which contains a test strip, a window for viewing test results and a well/opening separate from the window, having a top and serving for deposit of the sample; and
   b. a cap/cover means for sealing the top of the sample well/opening in a fluid tight relationship following deposit of the sample,
   c. the cartridge/cassette means containing a second test strip, a second window, for viewing test results and a second well/opening having a top and serving for deposit of the sample, whereby there are two well/openings whose tops are sealed by the cap/cover means in a fluid tight relationship following deposit of the sample.

18. An assaying device as claimed in claim 17, said two well/openings being connected by a channel.

19. An assaying device for depositing and analyzing a sample, comprising:
   I. a cartridge/cassette having a broad, lateral face (1a), a narrow, lateral face (1b), and a narrow end face (1c);
   A. the cartridge/cassette containing a test strip, a window in the broad, lateral face for viewing test results and, separate from the window, a well consisting essentially of an empty chamber in the broad, lateral face to serve for deposit of the sample; and II. a cap/cover means for covering and sealing the well in a fluid tight relationship following deposit of the sample the cap/cover means when sealing the top of the sample well/opening completely encircling the cartridge/cassette means, in order to hold the cap/cover means in a fluid tight relationship against the well.

20. In a device having:

I. a cartridge/cassette having a broad, lateral face (1a), a narrow, lateral face (1b), and a narrow end face (1c);
  A. the cartridge/cassette containing
    i. a test strip for the immunoassay method called antigen-antibody competitive binding to test a urine sample for drug use,
    ii. a window in the broad, lateral face for viewing test results and, separate from the window,
    iii. a well in the broad, lateral face to serve for deposit of the sample; the improvement comprising:

II. a cap/cover means for covering and sealing the well in a fluid tight relationship following deposit of the sample the cap/cover means when sealing the top of the sample well/opening completely encircling the cartridge/cassette means, in order to hold the cap/cover means in a fluid tight relationship against the well.

\* \* \* \* \*